United States Patent
Ilan

(10) Patent No.: US 10,611,821 B2
(45) Date of Patent: Apr. 7, 2020

(54) METHODS FOR TREATING OR REDUCING LIVER DISEASES BY ADMINISTERING ORAL COMPOSITION COMPRISING TNF RECEPTOR FUSION PROTEINS

(71) Applicant: HADASIT MEDICAL RESEARCH SERVICES & DEVELOPMENT LTD., Jerusalem (IL)

(72) Inventor: Yaron Ilan, Jerusalem (IL)

(73) Assignee: HADASIT MEDICAL RESEARCH SERVICES & DEVELOPMENT LTD., Jerusalem (IL)

( * ) Notice: Subject to any disclaimer, the term of this patent is extended or adjusted under 35 U.S.C. 154(b) by 0 days.

(21) Appl. No.: 14/856,582

(22) Filed: Sep. 17, 2015

(65) Prior Publication Data
US 2016/0002312 A1    Jan. 7, 2016

Related U.S. Application Data

(63) Continuation-in-part of application No. 14/198,603, filed on Mar. 6, 2014, now abandoned.

(60) Provisional application No. 61/773,314, filed on Mar. 6, 2013.

(51) Int. Cl.
| | | |
|---|---|---|
| A61K 38/17 | (2006.01) | |
| A61K 31/00 | (2006.01) | |
| C07K 14/715 | (2006.01) | |

(52) U.S. Cl.
CPC .......... *C07K 14/7151* (2013.01); *A61K 31/00* (2013.01); *A61K 38/1793* (2013.01); *C07K 2319/30* (2013.01)

(58) Field of Classification Search
CPC ....................... C07K 14/7151; C07K 2319/30; A61K 31/00; A61K 38/1793
See application file for complete search history.

(56) References Cited

U.S. PATENT DOCUMENTS

| | | | |
|---|---|---|---|
| 4,239,754 A | 12/1980 | Sache et al. | |
| 4,925,673 A | 5/1990 | Steiner et al. | |
| 5,405,855 A | 4/1995 | Andrulis | |
| 5,871,753 A | 2/1999 | Crabtree et al. | |
| 5,879,681 A | 3/1999 | Leone-Bay et al. | |
| 2003/0148955 A1 | 8/2003 | Pluenneke | |
| 2004/0126372 A1* | 7/2004 | Banerjee | C07K 16/241 424/145.1 |
| 2006/0083714 A1 | 4/2006 | Warner | |
| 2008/0025986 A1* | 1/2008 | Ozes | A61K 38/28 424/145.1 |
| 2008/0299196 A1 | 12/2008 | Nilsson et al. | |
| 2009/0074794 A1 | 3/2009 | Heavner et al. | |
| 2013/0216742 A1* | 8/2013 | DeMartino | A61J 1/00 428/34.4 |

OTHER PUBLICATIONS

Boetticher et al. A randomized, double-blinded, placebo-controlled multicenter trial of etanercept in the treatment of alcoholic hepatitis. Gastroenterology. Dec. 2008;135(6):1953-60.*
Liver Diseases, in MeSH Database, National Center for Biotechnology Information, Bethesda, Maryland, USA [online], [retrieved on May 21, 2017]. Retrieved from the Internet: <URL: https://www.ncbi.nlm.nih.gov/mesh/68008107>.*
Morishita et al. Is the oral route possible for peptide and protein drug delivery? Drug Discov Today. Oct. 2006;11(19-20):905-10. Epub Sep. 7, 2006.*
Worledge KL, Godiska R, Barrett TA, Kink JA. Oral administration of avian tumor necrosis factor antibodies effectively treats experimental colitis in rats. Dig Dis Sci. Dec. 2000;45(12):2298-305.*
Office Action for U.S. Appl. No. 14/198,603, dated Jun. 18, 2015.
Hirsch Jules "The search for new ways to treat obesity" Proc Natl Acad Sci U S A. Jul. 9, 2002; 99(14): 9096-9097.
Marx Jean "Obesity gene discovery may help solve weighty problem" Science. Dec. 2, 1994;266(5190):1477-8.
Van Deventer S.J.H "Transmembrane TNF-alpha, induction of apoptosis, and the efficacy of TNF-targeting therapies in Crohn's disease." Gastroenterology. Nov. 2001;121(5):1242-6.
Stephen C. et al. "Signals that regulate food intake and energy homeostasis" Science. May 29, 1998; 280(5368):1378-83.
Ilan, Y. "novel methods for the treatment of non-alcoholic steatohepatitis—targeting the gut immune system to decrease the systemic inflammatory response without immune suppression." *Alimentary pharmacology & therapeutics* 44.11-12 (2016): 1168-1182.
Ilan, Yaron. "Immune therapy for nonalcoholic steatohepatitis: are we there yet?." *Journal of clinical gastroenterology* 47.4 (2013): 298-307.

* cited by examiner

*Primary Examiner* — Robert S Landsman
(74) *Attorney, Agent, or Firm* — Pearl Cohen Zedek Latzer Baratz LLP

(57) ABSTRACT

This application describes a method of delivering a TNF antagonist molecule, in a biologically active form, to a subject in need thereof, the method comprising, orally or mucosally administering to the subject a therapeutically effective amount of a TNF antagonist molecule.
This application further describes a method of treating, preventing or reducing liver diseases, the method comprising, administering to the subject a therapeutically effective amount of a TNF antagonist molecule.

5 Claims, 3 Drawing Sheets

* p<0.07

* p<0.055

* p<0.008

METHODS FOR TREATING OR REDUCING LIVER DISEASES BY ADMINISTERING ORAL COMPOSITION COMPRISING TNF RECEPTOR FUSION PROTEINS

CROSS-REFERENCE TO RELATED APPLICATIONS

This application is a continuation-in-part of U.S. patent application Ser. No. 14/198,603, now abandoned, filed on Mar. 6, 2014, which claims the benefit of U.S. Provisional Patent Application No. 61/773,314, filed Mar. 6, 2013, which are hereby incorporated by reference.

BACKGROUND OF THE INVENTION

Tumor necrosis factor (TNF), a naturally occurring cytokine, plays a central role in the inflammatory response and in immune injury. TNF is formed by the cleavage of a precursor transmembrane protein, forming soluble molecules, which aggregate to form trimolecular complexes. These complexes bind to receptors found on a variety of cells. The binding of TNF causes many pro-inflammatory effects, including release of other pro-inflammatory cytokines, such as interleukin IL-6, IL-8, and IL-1; release of matrix metalloproteinases; and upregulation of the expression of endothelial adhesion molecules, further amplifying the inflammatory and immune cascade by attracting leukocytes into extravascular tissues. TNF was found to have a main role in the pathogenesis of several immune mediated disorders, among them rheumatoid arthritis (RA) and Crohn's Disease. TNF alpha may have a role in the gut in various local inflammatory and infectious disorders. It is known that high levels of the pro-inflammatory cytokines, interleukin-1beta (IL-1beta) and tumor necrosis factor-alpha (TNF-alpha), are present in the gut mucosa of patients suffering form various diseases, in particularly inflammatory bowel diseases (IBD).

Specific TNF inhibitors/antagonists were developed, such as infliximab, a chimeric anti-TNF monoclonal antibody (mAb), which showed significant effect in treating Crohn's Disease and RA, as well as etanercept, a recombinant fusion protein consisting of two soluble TNF receptors joined by the Fc fragment of a human IgG1 molecule, which was found effective in the treatment of treating RA and psoriatic Arthritis. Other TNF blockers are pegylated soluble TNF Receptor Type I (PEGs TNF-R1), other agents containing soluble TNF receptors, CDP571 (a humanized monoclonal anti-TNF-alpha antibodies), thalidomide, phosphodiesterase 4 (IV) inhibitor thalidomide analogues and other phosphodiesterase IV inhibitors.

This therapeutic potential of TNF antagonists and anti TNF alpha receptor is based on the fact that TNF-alpha is the main mediator of the inflammatory response in many organ systems.

Various researches showed that all TNF inhibitors are immunosuppresssants.

Parenterally administered soluble anti TNF alpha receptor is being used or was tested in the treatment of various TNF dependent inflammatory disorders, such as stomatitis, rheumatoid, juvenile rheumatoid and psoriatic arthritis, plaque psoriasis and ankylosing spondylitis. Further the effect of TNF antagonists was assessed in the the following diseases/conditions: demyelinating diseases, neurodegenerative diseases, trauma, injuries and the like.

Oral administration, which is non-invasive, provides many advantages: ease and convenience of use, improved patient acceptance and compliance, high degree of vascularization, relatively lengthy retention time, natural disposal of inactive, non-metabolized ingredients, direct contact with the gastrointestinal organs.

Oral administration of anti TNF or of the TNF receptor fusion protein also carries an advantage of using the unique ability of the immune system of the gut to induce regulatory T-Cells (Tregs) or to alter the systemic immune system in specific ways that are different and more effective than by intravenous administration. In addition, oral administration may alter the systemic immune paradigm suppressing inflammation without exposing the patient to a general immune suppression and therefore to severe infections or malignancies that are known to be associated with the intravenous route of treatment of anti TNF compounds.

Currently, there is no oral TNF antagonist or anti TNF alpha receptor in the market due to the high acidity and enzymatic degradation in the stomach that inactivates or destroys the molecule before reaching the blood circulation. There is a need for an oral composition comprising a TNF antagonist that overcomes the above described drawbacks.

There is further a need to improve the efficacy of TNF antagonists in the treatment of inflammation, diseases associated with inflammation and other diseases, by preventing bacterial translocation and by inducing systematic regulatory cells.

SUMMARY OF THE INVENTION

In an embodiment of the invention, there is provided a method of delivering a TNF antagonist molecule, in a biologically active form, to a subject in need thereof, the method comprising, orally or mucosally administering to the subject a therapeutically effective amount of a TNF antagonist molecule.

In another embodiment, there is provided a dosage form for delivery of a TNF antagonist to the GI organs of a subject, the dosage form comprising, a therapeutically effective amount of a TNF antagonist molecule.

In some embodiments, there is provided a method for treating or preventing or reducing the severity of a disease in a subject-in-need thereof, the method comprising enterally or mucosally administering to the subject a therapeutically effective amount a TNF antagonist thereby treating or preventing or reducing the severity of a disease.

In some embodiments, the disease is a chronic liver disease.

In some embodiments of the invention, there is provided a method of treating, preventing or reducing the severity of obesity, the method comprising, administering to the subject a therapeutically effective amount of a TNF antagonist molecule.

In some embodiments of the invention, there is provided a method of inducing an overall weight loss in a subject or maintaining a constant weight with a diet enriched in carbohydrates or fats, without changing the eating habits, the method comprising administering to the subject a therapeutically effective amount of a TNF antagonist molecule. This is exemplified in Example 1, in which mice that were treated with ETANERCEPT for nine days showed a significant loss in the weight in comparison to control mice.

In some embodiments, there is provided a method of treating, reducing or preventing the effect of a medicines that causes liver intoxication, such as for example, acetaminophen on the liver by administering to the subject in need a therapeutically effective amount of TNF antagonist, thereby treating, reducing or preventing the effect of acetaminophen on the liver.

In The TNF antagonist may be administered sequentially or simultaneously or prior to the addition of the medicine that causes intoxication.

In an embodiment of the invention, there is provided a method for treating or preventing or reducing liver diseases in a subject in need thereof, the method comprising orally administering to the subject a therapeutically effective amount of pharmaceutical composition in a form of a liquid comprising a TNF antagonist thereby treating or preventing or reducing the severity of the liver disease.

In some embodiments, the liquid is water.

In some embodiments, the composition further comprises a preservative.

In some embodiments, the preservative is benzyl alcohol.

In some embodiments, the TNF antagonist is an anti TNF alpha receptor.

In some embodiments, the anti TNF alpha receptor is etanercept.

In some embodiments, the disease is a chronic liver disease.

In some embodiments, the disease is fatty liver disease.

In some embodiments, the disease is non alcoholic fatty liver disease (NAFLD).

In some embodiments, the disease is NASH.

In some embodiments, the disease is fibrosis.

In some embodiments, the disease is cirrhosis.

In some embodiments, the disease is alcoholic liver disease (ALD).

In some embodiments, the disease is hepatitis.

In some embodiments, the disease is hepatitis A, B or C.

In an embodiment of the invention, there is provided a pharmaceutical composition for oral administration comprising an effective amount of TNF antagonist for treating or preventing or reducing liver diseases in a subject in need thereof In some embodiments, the pharmaceutical composition is in the form of a liquid.

In some embodiments, the liquid is water.

In some embodiments, the TNF antagonist is an anti TNF alpha receptor.

In some embodiments, the anti TNF alpha receptor is etanercept.

DETAILED DESCRIPTION OF THE INVENTION

Figure 1:
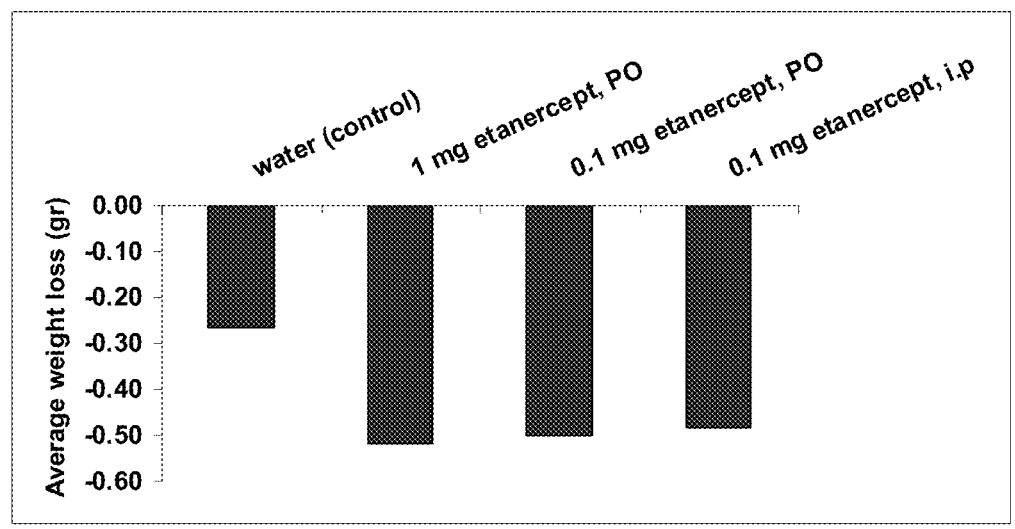
FIG. 1 is a bar graph describing the weight loss (in grams) of mice treated with ETANERCEPT in comparison to control mice.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The invention relates to methods and compositions for the administration of TNF antagonist, which may be anti TNF alpha receptor. More particularly, this invention is directed to a form of the TNF antagonist Etanrecept, that may be administered enetrally (oral) or via mucosal administration so as to treat or prevent or reduce the severity of diseases that are associated with TNF, autoimmune diseases or diseases associated with inflammatory diseases.

In some embodiments, the TNF antagonist molecule is anti TNF alpha receptor. In some embodiments, the anti TNF alpha receptor is Etanercept.

The terms "TNF antagonist, TNF inhibitor, TNF blocker, anti TNF or anti TNF molecule, biomolecule or compound" interchangeably refer herein to any compound that prevents or inhibits the binding of TNF to its receptor and includes specific TNF inhibitors/antagonists, such as infliximab, a chimeric anti-TNF monoclonal antibody (mAb), which showed significant effect in treating Crohn's Disease and RA, as well as Etanercept, a recombinant fusion protein consisting of two soluble TNF receptors joined by the Fc fragment of a human IgG1 molecule, which was found effective in the treatment of RA and psoriatic Arthritis. Other TNF blockers are pegylated soluble TNF Receptor Type I (PEGs TNF-R1), other agents containing soluble TNF receptors, CDP571 (a humanized monoclonal anti-TNF-alpha antibodies), thalidomide, phosphodiesterase 4 (IV) inhibitor thalidomide analogues and other phosphodiesterase IV inhibitors.

As used herein, the term "antibody" is meant to refer to complete, intact antibodies, and Fab fragments, scFv, and F(ab).sub.2 fragments thereof. Complete, intact antibodies include monoclonal antibodies such as murine monoclonal antibodies (mAb), chimeric antibodies, humanized antibodies and human. The production of antibodies and the protein structures of complete, intact antibodies, Fab fragments, scFv fragments and F(ab).sub.2 fragments and the organization of the genetic sequences that encode such molecules, are well known and are described, for example, in Harlow et al., ANTIBODIES: A LABORATORY MANUAL, Cold Spring Harbor Laboratory, Cold Spring Harbor, N.Y. (1988) and Harlow et al., USING ANTIBODIES: A LABORATORY MANUAL, Cold Spring Harbor Press, 1999, which are herein incorporated by reference in their entirety.

"Epitope" refers to a region on an antigen molecule to which an antibody or an immunogenic fragment thereof binds specifically. The epitope can be a three dimensional epitope formed from residues on different regions of a protein antigen molecule, which, in a naive state, are closely apposed due to protein folding. "Epitope", as used herein, can also mean an epitope created by a peptide or hapten portion of TNF-alpha and not a three dimensional epitope. Preferred epitopes are those wherein when bound to an immunogen (antibody, antibody fragment, or immunogenic fusion protein) result in inhibited or blocked TNF-alpha activity.

"TNF-alpha blocking" refers to a compound or composition that blocks, inhibits or prevents the activity of TNF or TNF-alpha.

Compounds that possess TNF-alpha inhibitory activity are for example tetracyclines, (e.g., tetracycline, doxycycline, lymecycline, oxytetracycline, minocycline), and chemically modified tetracyclines (e.g., dedimethylamino-tetracycline), hydroxamic acid compounds, carbocyclic acids and derivatives, thalidomide, lazaroids, pentoxifylline, napthopyrans, soluble cytokine receptors, monoclonal antibodies towards INF-alpha, amrinone, pimobendan, vesnarinone, phosphodiesterase inhibitors, lactoferrin and lactoferrin derived analogs, melatonin, norfloxacine, ofloxacine, ciprofloxacine, gatifloxacine, pefloxacine, lomefloxacine, temafloxacine, TTP and p38 kinase inhibitors.

Other TNF inhibitors are specific TNF inhibitors Monoclonal antibodies such as: infliximab, CDP-571 (HUMICADE™), D2E7 (Adalimumab), and CDP-870; Polyclonal antibodies; Soluble cytokine such as: receptors etanercept, lenercept, pegylated TNF receptor type 1, and TBP-1; TNF receptor antagonists; Antisense such as: oligonucleotides.

In an embodiment of the invention, there is provided a method of treating, preventing or reducing the severity of obesity by administering to the subject a therapeutically effective amount of a TNF antagonist.

In some embodiments of the invention, there is provided a method of treating, preventing or reducing the severity of obesity by parenterally or orally administering to the subject in need a therapeutically effective a TNF antagonist.

In some embodiments of the invention, there is provided a method of treating, preventing or reducing the severity of obesity by enterally or mucosally administering to the subject a therapeutically effective amount a TNF antagonist.

The immune system and the regulation of adipose tissue metabolism appear to be closely interlinked. Up to fifty percent of cells within adipose tissues are composed of non-adipose cells, including many immunocytes. Most of the research in the field has been focused on the immunological consequences of morbid obesity. Immunological alterations that are known to exist in obese animals and humans include reduced DTH and mitogen-stimulated lymphocyte proliferation responses, impaired phagocyte number and function, attenuation of insulin induced lymphocyte cytotoxicity, and changes in the CD4/CD8 ratio, especially during weight loss attempts.

Adipose cells are known to secrete pro-inflammatory cytokines including TNF-β and IL6, which are both related to the level of adiposity. Some of these cytokines are considered to have metabolic effects such as insulin resistance mediated by TNF-β and lipoprotein lipase inhibition mediated by IL6. TNF-β knockout mice have a higher insulin sensitivity and an improved lipid profile in comparison to their normal littermates. Other components of the immune system, which are produced by adipose cells, include the protein adipsin, which is an integral part of the alternative complement system, and functions identically to human complement factor D.

Several recent studies suggest that the immune system may have an important contributory role in the development of obesity. Several cytokines are known to act as adipose tissue regulators. TNF-β suppresses the expression of β3 adreno-receptors on adipose cells, which are involved in sympathetically mediated lipolysis, while IL1 stimulates adipose leptin secretion. The metabolic activity rate of adipose cells has been observed to be closely correlated to their distance from the closest lymph node through a mechanism which is partly mediated by IL4, IL6 and TNF-β. The changes in inflammatory status of adipose tissue and liver with obesity suggest that obesity represents a state of chronic low-level inflammation. Various molecular mechanisms have been implicated in obesity-induced inflammation.

The use of a TNF antagonist in the treatment of obesity has not been demonstrated to date.

However, it is believed that oral delivery of a TNF antagonist, such as an anti TNF alpha receptor, may be used for the treatment of obesity by decreasing the inflammatory mechanism associated with obesity whether in the gut or systemically.

Further, a treatment of obesity by administrating TNF antagonists is expected to exert a beneficial therapeutic effect due to prolonged exposure and better presentation of TNF antagonists to the gut immune system, by the mechanisms explained herein.

The invention is further related to the treatment of diseases that are associated or augmented by bacterial translocation and or gut flora derangement, such as, for example, without being limited, chronic liver diseases and Alzheimer disease, hepatic encephalopathy, ADHD, metabolic syndrome, diabetes both type 1 and type 2, atherosclerosis or chronic fatigue syndrome, NASH, obesity, hepatic encephalopathy and potentially several immune mediated disorders among them Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection, by the enetral or mucosal administration of biologically active TNF antagonists.

The invention is further related to the induction of systemic regulatory cells whether they are CD4+CD25+ Foxp3+ or any other type of regulatory cells or suppressive cell, including, but not limited to, LAP+ cells, IL10 secreting cells, TGFbeta secreting cells, by the enetral or mucosal administration of biologically active TNF antagonists. These systemic regulatory cells may augment the effect of TNF antagonists in treating diseases associated with inflammation in comparison to the effect of parenteral TNF antagonists. The augmentation of the effect can be via the induction of suppressive cells, or via any other method that decreases the number or suppresses the function of pro inflammatory cells, or decreases the secretion of pro inflammatory cytokines, or acts by altering antigen presentation to professional or non professional antigen presenting cells. Any of these mechanisms will further augment the effect of anti TNF when administered orally in comparison with intravenous administration. In addition, specific administration of anti TNF alpha antagonists may also work via specific mechanisms that are promoted by binding to TNF in the gut, or to TNF expressed on different types of cells in the gut, thereby altering the systemic immune system by several mechanisms.

In an embodiment of the invention, there is provided a dosage form for delivery of a TNF antagonist into the gastrointestinal (GI) organs of a subject, the dosage form comprising a TNF antagonist.

The invention further provides a method for treating or preventing or reducing the severity of a disease in a subject in need thereof, the method comprising enterally or mucosally administering to the subject a therapeutically effective amount of a TNF antagonist thereby treating or preventing or reducing the severity of a disease.

In some embodiments of the invention, the disease is related to gastrointestinal inflammation and may be inflammatory bowel disease (IBD), ulcerative colitis (UC) or Crohn's disease (CD).

Inflammatory bowel disease (IBD), a form of chronic gastrointestinal inflammation, includes a group of chronic inflammatory disorders of generally unknown etiology, e.g., ulcerative colitis (UC) and Crohn's disease (CD).

Immunosuppressive and anti-inflammatory agents in high maintenance doses are the principal drugs used in the therapy of chronic inflammatory gastrointestinal disorders. Specific anti-TNF antibodies have also been used for treatment of IBD. About 20-25% of the patients with UC failed to respond to intensive and optimal medical therapy. In general, patients with CD are less responsive to medical therapy and usually do not respond to surgical treatment. Anti-TNF alpha antibodies have also been introduced to treat patients with CD with some efficacy, but this treatment is ineffective in patients with UC.

Oral administration of anti TNF or of Etanercept may have at least equally therapeutic effect to that of intravenous administration, preventing the unwanted side effects of an invasive procedure. Oral administration may also have a more profound effect than that of the intravenous route, by inducing any of the above described mechanisms. In addition, oral administration may alter the systemic immune paradigm suppressing inflammation without exposing the patient to a general immune suppression and therefore to sever infections, or malignancies that are known to be associated with the intravenous route of treatment of anti TNF compounds.

The method of treating, preventing or reducing the severity of IBD, CD or UC by enterally or mucosally administering to the subject a therapeutically effective amount of a TNF antagonist is expected to be beneficial due to the directed administration to the GI in comparison to parental treatments with TNF antagonists and with other oral compositions comprising TNF antagonists.

Oral administration of anti TNF compounds according to the invention have prolonged exposure and better presentation of the anti TNF compounds to the gut immune system. It may also have less systemic side effects.

The above can be achieved by at least one of the following potential mechanisms:

Induction of regulatory T cells, which suppress inflammation without the induction of generalized immune suppression thus decreasing the unwanted side effects associated with intravenous administration, among them malignancies and severe infections.

Oral administration may alter the Th1 Th2 immune paradigm.

Oral administration can suppress the secretion of pro inflammatory cytokines in a more profound way by activating specific mechanisms in the gut associated immune system.

Any of the above, as well as other potential mechanism may also explain why the anti TNF compounds in an oral form, anti TNF compounds can exert a more profound effect on the immune system for suppressing inflammation at the target of the disease, but at the same time, not induce generalized immune suppression state that is induced by the intravenous route, thereby omitting the unwanted side effects associated with the intravenous administration of anti TNF including exposure to malignancies, severe generalized infections, tuberculosis and others.

In another embodiment of the invention, there is provided a method for treating or preventing or reducing the severity of a disease or disorder that involves an inflammation in the gut whether infectious or inflammatory, including but is not limited to, bacterial, viral, fungal infections in a subject-in-need thereof, the method comprising enterally or mucosally administering to the subject a therapeutically effective amount of a TNF antagonist, thereby treating or preventing or reducing the severity of the disease or the disorder. In an embodiment of the invention the disease is Celiac disease, Behchet disease, vasculitis, Whipples disease, NASH, obesity, degenerative neurological disorders, Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

The gut immune system is challenged to respond to pathogens while remaining relatively unresponsive to food antigens and the commensal microflora. The gut immune system can differentiate the antigenic signals of parasites from the high background noise of food and bacterial antigens. The tight regulation that is required to maintain homeostasis and is based on multiple immune factors. Immune mechanisms involve both innate responses, mediated particularly by NK cells, NKT cells, dendritic cells, macrophages, and polymorphonuclear cells, and adaptive cellular and humoral immunity, mediated by T and B lymphocytes. Lymphocytes that mediate the adaptive immune response are primarily located in the epithelium (intraepithelial lymphocytes), lamina propria, and Peyer's patches. B-cells produce immunoglobulins, primarily of the IgA type. The unique structure of the gut mucosa immune system makes it an attractive site for manipulation of the immune system including for promoting regulatory T-cells (Tregs) as a means of treating immune-mediated disorders.

Gut-associated lymphoid tissue (GALT) comprises several organs and departments: Peyers patches (PPs) (the appendix, and isolated lymphoid follicles (ILFs), which are considered to be inductive sites for mucosal B- and T-cells. The occurrence of other GALT-like elements, such as lymphocyte-filled villi and cryptopatches, is species-dependent, and these structures do not appear to be involved in B-cell induction. Any of the above cells may play a role in the systemic induction of anti inflammatory state via oral administration of anti TNF compounds.

Thus, in an embodiment of the invention, there is provided a method of inducing of regulatory suppressor cells systemically by enterally or mucosally administering to the subject a therapeutically effective amount of a TNF antagonist, thereby inducing regulatory suppressor T cells systemically. Regulatory cells can be both the classical CD4+ CD25+Foxp3+ and non classical or other suppressor cells including Th1 cells, LAP+ cells, NKT cells, or any other subsets of T or B cells.

According to this embodiment, any type of inflammatory disorder whether associated with TNF antagonist or not can be treated by the method described herein.

In an embodiment of the invention, there is provided a method of treating, preventing or reducing the severity of chronic liver disease by enterally or mucosally administering to the subject a therapeutically effective amount of a TNF antagonist, thereby treating, preventing or reducing the severity of chronic liver disease. In an embodiment of the invention, the chronic liver disease is fatty liver disease including non alcoholic steatohepatitis (NASH).

In some embodiments of the invention, there is provided a method of treating, reducing or preventing the a medicine that causes liver intoxication by administering to the subject in need a therapeutically effective amount of TNF antagonist, thereby treating, reducing or preventing the effect of the medicine on the liver.

The TNF antagonist may be administered sequentially or simultaneously or prior to the addition of the medicine that causes liver intoxication that may be in some embodiments, acetaminophen.

In some embodiments, the TNF antagonist is administered parenterally.

In some embodiments of the invention, there is provided a method of treating, reducing or preventing the effect of medicine that causes liver intoxication by administering to the subject in need a therapeutically effective amount of a TNF antagonist, thereby treating, reducing or preventing the effect of the medicine that causes liver intoxication that maybe in some embodiments acetaminophen.

In an embodiment of the invention, there is provided a method of treating, preventing or reducing the severity of a disorder related to bacterial translocation (BT) whether it depends on a TNF antagonist mechanism or not, such as neurological disorders including Alzheimer disease, hepatic encephalopathy, ADHD, metabolic syndrome, diabetes both type 1 and type 2, atherosclerosis or chronic fatigue syndrome by enterally or mucosally administering to the subject a therapeutically effective amount of a TNF antagonist, thereby treating, preventing or reducing the severity of the disorder associated with BT.

The rational for these embodiments relies on the relation between bacterial translocation (BT) and chronic liver disease: gut flora and BT play an important role in the pathogenesis of chronic liver disease, including cirrhosis and its complication. Pre clinical and clinical studies over the last decade suggested a role for BT in the pathogenesis of non alcoholic steatohepatitis (NASH). BT and derangement of gut flora is of substantial clinical relevance to patients with chronic liver disease and cirrhosis. Intestinal bacterial overgrowth and increased bacterial translocation of gut flora from the intestinal lumen, in particular, predispose to an increased potential for bacterial infections and major complication in these patients. Levels of bacterial lipopolysaccharide (LPS), a component of Gram-negative bacteria, are increased in the portal and/or systemic circulation in several types of chronic liver diseases. Impaired gut epithelial integrity via alterations in tight junction proteins, increased gut permeability and increase LPS levels were described in patients with alcoholic and non alcoholic steatohepatitis. Increased serum LPS levels and activation of the pro-inflammatory cascade may also be important in disease progression in these settings.

Thus, prevention of gut flora derangement and BT by the administration of a TNF antagonist will prevent the development and or the progress of chronic liver disorder as well as a disorder related to bacterial translocation (BT) whether it depends on a TNF antagonist mechanism or not, such as neurological disorders including Alzheimer disease, hepatic encephalopathy, ADHD, metabolic syndrome, diabetes both type 1 and type 2, atherosclerosis or chronic fatigue syndrome.

Oral administration of the anti TNF compounds in the form of cells can further increase the effect of the oral route by any of the following: inducing prolonged presentation, activating different types of cells in the gut immune system, and altering the downstream mechanisms associated with the anti TNF.

Inflammation is a pathogenic component of various types of immune mediated disorders, and it contributes to progressive damage in many organs. Systemic inflammation and chronic damage are mediated by the innate immune response which is regulated by Toll-like receptors (TLR). Cells of the innate immune system can both initiate and maintain inflammation in the liver. Lymphocytes are activated after interacting at the mesenteric lymph nodes (MLNs) with bacteria translocated from the gut. Systemic activation of the inflammatory immune system contributes to the progression of many disorders. BT starts a Th1 immune response in MLNs involving Th1 polarization and monocyte activation to TNF-alpha production. The recirculation of these activated effector immune cells into blood promotes systemic inflammation. This may be applicable to any of the following disorders whether TNF plays a direct role in their pathogenesis or not, as the promotion of Tregs, for example, can suppress inflammation irrespective of the mechanism of the inflammation.

Toll-like receptors (TLRs) recognize pathogen-associated molecular patterns (PAMPs) to detect the presence of pathogens. TLRs are expressed on both immune cells, Kupffer cells, endothelial cells, dendritic cells, biliary epithelial cells, hepatic stellate cells, and hepatocytes. TLR signaling induces potent innate immune responses in these and other cell types.

TLRs also play a role in the regulation of inflammation based on their ability to recognize endogenous TLR ligands termed damage-associated molecular patterns (DAMPs).

Oral route of administration of anti TNF may alter the function of any of the above mechanisms, thereby further enhancing their effects.

The systemic effect of oral administration of soluble TNF antagonist can lead to alleviation of immune mediated disorders, and to the alleviation of disorders in which the immune system play some role, whether the TNF antagonist plays a role or not, by different mechanisms than induction of Tregs, such as alteration of TLRs downstream pathways, induction of specific cells in the GALT, of induction of secretion of cytokines or chemokines whether directly or indirectly.

Examples of immune mediated disorders include, but are not limited to, Obesity, NASH, degenerative neurological disorders, chronic fatigue syndrome, Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

As used herein, a "pharmaceutical composition" refers to a preparation of one or more of the active ingredients described herein with other chemical components such as physiologically suitable carriers and excipients.

The pharmaceutical compositions can take the form of solutions, suspensions, emulsions, tablets, or capsules. The pharmaceutical compositions can also take the form of powders, enteric coated, sustained-release formulations and the like. The compositions can be formulated with traditional binders and carriers such as triglycerides, microcrystalline cellulose, gum tragacanth or gelatin. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of TNF antagonist, preferably in a substantially purified form, together with a suitable amount of carrier so as to provide the form for proper administration to the subject.

The amount of a source of the TNF antagonist, which will be effective in the treatment of a particular disorder or condition will depend on the nature of the disorder or condition and on the TNF antagonist, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to the ingredients of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For enteric coated compositions, the coating composition typically contains an insoluble matrix polymer and a water soluble material. An enteric polymer may be used. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups. Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 are used to deliver biologically active agents orally are known in the art.

Non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. In such preparations, the active ingredient is slowly released from the particles by diffusion or following slow erosion of the particles in the stomach.

Suitable non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the Eudragit brand polymers. Other film-forming materials may be used alone or in combination with each other or with the ones listed above. These other film forming materials generally include poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Various aspects of the invention are described in greater detail in the following Examples, which represent embodiments of this invention, and are by no means to be interpreted as limiting the scope of this invention.

EXAMPLES

Example 1

Measurement of the Effect of ENBREL® (ETANERCEPT) on Weight Loss
Methods:
Medicine Preparation: One ampoule of ETANERCEPT containing 25 mg was dissolved with 1 ml of vehicle (=25 mg/ml, 2500 µg/1000 µl) according to the manufacturer's instructions.

Animals: Male C57BL/6 (B6) mice (12-13 weeks old) were purchased from Harlan Laboratories (Jerusalem, Israel). All mice were maintained in specific pathogen-free conditions. Mice were maintained in the Animal Core of the Hadassah-Hebrew University Medical School. All mice were administered standard laboratory chow and water ad libitum and kept in a 12-hour light/dark cycle.

Experiment Protocol: Four groups (six mice per group) were included in the following experiment.
Group A: Control mice, per oz. administration of 30 µl water.
Group B: Per oz. (PO) administrations of 1 mg of ETANERCEPT.
Group C: PO administrations of 0.1 mg of ETANERCEPT.
Group D: i.p administrations of 0.1 mg of ETANERCEPT.

Treatment was for six consecutive days, followed by one day without treatment after which the mice were treated for another three consecutive days.

Mice were daily weighed and all mice were sacrificed on the $9^{th}$ day.

Weight was calculated as follows: weight differences were calculated by subtracting the initial weight (one day before treatment) of every mouse, from its weight on day 9. Then the average mean of 'weight differences' for every group was calculated. Results are presented in Table 1 and in FIG. 1

TABLE 1

Effect of ETANERCEPT on mice weight

| Group | Weight before treatment (day 0) | Weight after treatment (day 9) | Weight differences (gr) |
|---|---|---|---|
| Control (water) | 27.37 ± 1.16 | 27.10 ± 1.57 | −0.27 |
| PO, 1 mg of ETANERCEPT. | 25.05 ± 2.3 | 24.5 ± 2.3 | −0.55 |
| PO, 0.1 mg of ETANERCEPT | 26.37 ± 4.32 | 25.87 ± 4.23 | −0.55 |
| i.p, 0.1 mg of ETANERCEPT | 28.42 ± 1.12 | 27.93 ± 1.35 | −0.49 |

As can be seen, the pretreatment with ETANERCEPT in particularly when administered PO caused a dramatic effect on weight loss in the mice.

Example 2

Effect of ENBREL® (ETANERCEPT) in Concanvalin A (ConA) Model
Introduction:
Several animal models mimicking human liver injury are known to be applied for exploring the immunopathogenesis in liver diseases. However, an acceptable in vivo model for hepatitis C virus HCV does not exist, as HCV is a non cytopathic virus and its liver damage is immune mediated.

ConA Induced Hepatitis. The Concanvalin A (ConA) model is a widely utilized mouse model that mimics many aspects of human autoimmune hepatitis. ConA is a bean lectin, which when injected intravenously to mice, induces activation of lymphocytes in the liver. ConA induces massive liver necrosis in mice, simultaneously with the lymphocyte infiltration in the liver, high level of apoptotic hepatocytes and elevated serum alanine aminotransferase (ALT) and aspartate aminotransferase (AST). The activated lymphocytes in the liver injury were later on confirmed to be Natural Killer T (NKT) cells. Together with Kupffer cells, NKT cells secrete large amounts of various hepatotoxic cytokines, most notably IFN-γ and TNF-α. The immune-mediated liver injury which develops in the ConA model is very rapid: less than 24 hours. The peak for liver enzymes and proinflammtory cytokines is less then 15 h and therefore it is an efficient in vivo model for screening anti inflammatory agents. Here, using the ConA model, the efficacy of ETANERCEPT in the preventing of hepatic, immunologic disorder was demonstrated. The results clearly demonstrate an anti-inflammatory effect of ETANERCEPT.

Methods:

Medicine Preparation: One ampoule of ETANERCEPT containing 25 mg was dissolved with 1 ml of vehicle (=25 mg/ml, 2500 µg/1000 µl) according to the manufacturer's instructions.

Animals: Male C57BL/6 (B6) mice (12-13 weeks old) were purchased from Harlan Laboratories (Jerusalem, Israel). All mice were maintained in specific pathogen-free conditions. Mice were maintained in the Animal Core of the Hadassah-Hebrew University Medical School. All mice were administered standard laboratory chow and water ad libitum and kept in a 12-hour light/dark cycle. Each group of mice (four mice in a group) was administered with either 0.1 mg ETANERCEPT (treated mice) or 100 µl water (control).

Experiment Protocol: i.p administrations of 0.1 mg of ETANERCEPT (treated mice) and 100 µl water (control mice) were performed once a day for three consecutive days prior to ConA injection. Con A was purchased from MP Biomedicals (Ohio, USA). Con A (20 mg/kg) was dissolved in 200 µl of 50 mM Tris pH 7, 150 mM NaCl, 4 mM $CaCl_2$, and injected (500 µg/mouse) intravenously to tail vein of all mice. All mice were sacrificed after 14h. Sera from individual mice were obtained 14 h after ConA injection. The serum activities of ALT and AST were determined after 1:20 dilutions, using a Reflovet Plus clinical chemistry analyzer. Serum levels of IFN-γ were determined by "sandwich" ELISA using commercial kits (Quantikine, R&D Systems, Minneapolis, Minn., US), according to the manufacturer's instructions. After mice were sacrificed, livers and spleens from all mice were removed for the use of flow cytometry (FACS) in order to detect changes in the expression of hepatic and splenic markers (regulatory T cells, Tregs).

Isolation of Splenocytes and Intrahepatic Lymphocytes: Livers and spleens were removed after sacrifice and stored in RPMI-1640 supplemented with Fetal Calf Serum. Spleens were crushed through a 70-µm nylon cell strainer (Falcon) and centrifuged (1250 rpm for 7 min). Red blood cells were lysed in 1 ml of cold 155 mM ammonium chloride lysis buffer. Splenocytes were washed and resuspended in 1 ml of RPMI supplemented with FCS. The viability of cells as assessed by trypan blue exclusion exceeded 90%. For intrahepatic lymphocytes, livers were crushed through a stainless mesh (size 60, Sigma). Ten milliliters of Lymphoprep (Ficoll, Axis-Shield PoC AS, Oslo, Norway) was loaded with a similar volume of the cell suspension in 50-ml tubes. The tubes were centrifuged at 1800 rpm for 18 min. Cells present in the interface were collected and centrifuged again at 1800 rpm for 10 min to obtain a pellet of cells depleted of hepatocytes. Approximately $1 \times 10^6$ cells/mouse liver were recovered.

Flow Cytometry for Lymphocyte Subsets: Flow cytometry was performed following splenocyte and hepatic lymphocyte isolation using $1 \times 10^6$ lymphocytes in 100 µl PBS with 0.1% BSA. For surface staining, cells were incubated with fluorochrome-conjugated antibodies to the indicated cell surface markers (eBioscience, San Diego, Calif., USA) at the recommended dilutions or with isotype control antibodies for 30 minutes at 4° C. The following cell surface anti-mouse antibodies were used: CD4-FITC, CD25-PE and CD8-APC. Cells were then washed in PBS containing 1% BSA and fixed with fixation buffer (eBiosciences) for another 50 minutes. For intracellular staining of Foxp3, fixed cells were permeabilized with Foxp3 staining buffer (eBioscience). Cells were then stained with PE-Cy7-conjugated antibodies to Foxp3 (eBiosciences), washed twice and resuspended in 250 µl of PBS containing 1% BSA and kept at 4° C. One million stained cells in 250 µl of PBS containing 1% BSA were subsequently analyzed using a FACS LSR II instrument (Becton Dickinson, San Jose, Calif.) with FCS express V.3 software (DeNovo software, CA, USA). Only live cells were counted, and background fluorescence from non-antibody-treated lymphocytes was subtracted.

Results

Table 2 presents the effect of ETANERCEPT on the serum levels of the liver enzyme ALT.

TABLE 2

Effect on serum levels of ALT in ConA model

| Group | ALT (u/L) |
|---|---|
| Cont, water | 5680 ± 2850 |
| 0.1 mg ETANERCEPT | 698 ± 792 |

As can be seen from the above table, the administration of 0.1 mg of ETANERCEPT resulted in about 87% reduction in the serum levels of ALT, compared to the administration of water only (p<0.007).

Figure 2:
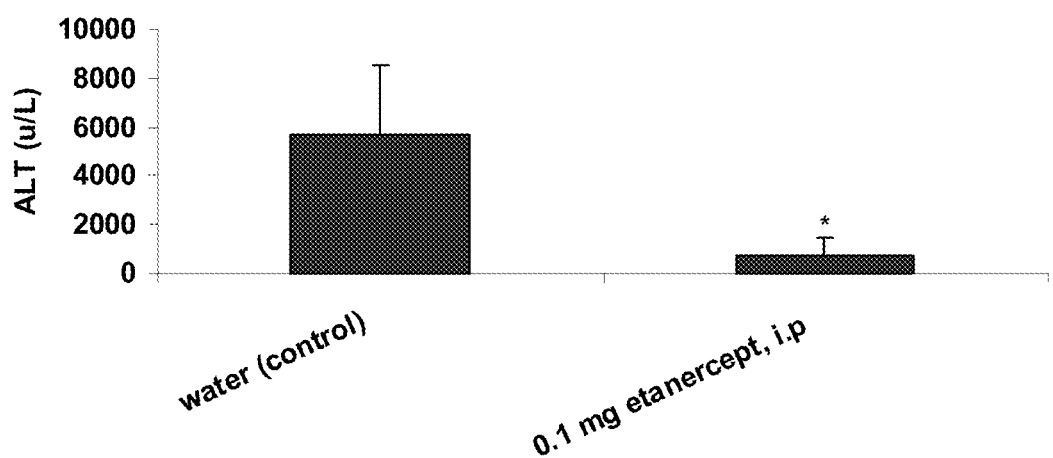
FIG. 2 is a bar graph showing that administration of 0.1 mg of ETANERCEPT resulted in about 87% reduction in the serum levels of ALT, in comparison to the administration of water only ($p<0.007$).

These results are also presented in FIG. 2.

TABLE 3

Effect on serum levels of IFN-γ in ConA model

| Group | IFN-g (pg/ml) |
|---|---|
| Cont, water | 1651.9 ± 783 |
| 0.1 mg ETANERCEPT | 676.5 ± 250 |

Figure 3:
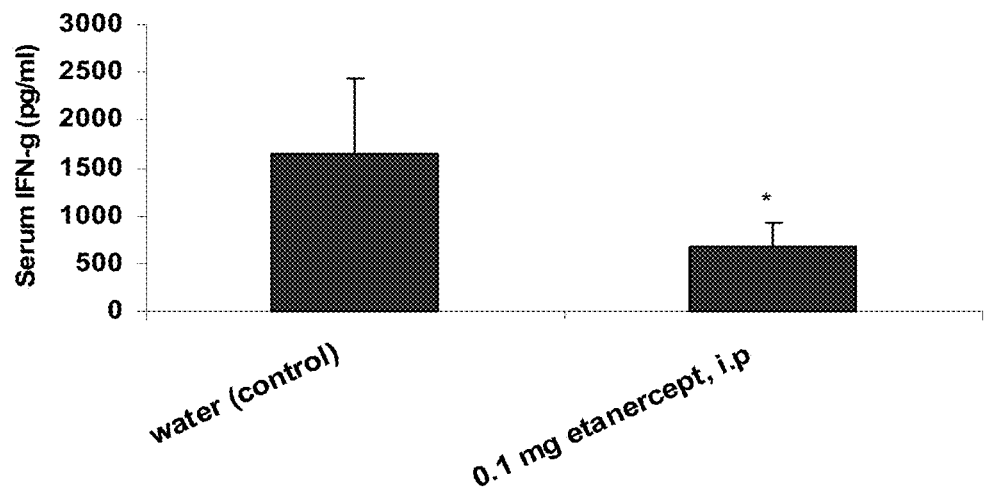
FIG. 3 is a bar graph showing that administration of 0.1 mg of ETANERCEPT resulted in about 59% reduction in the serum levels of IFN-γ as compared to the administration of water only ($p<0.055$).

As can be seen from the above table, administration of 0.1 mg of ETANERCEPT resulted in about 59% reduction in the serum levels of IFN-γ, compared to the administration of water only (p<0.055). These results are also presented in FIG. 3.

The Effect of ETANERCEPT on Hepatic Tregs in ConA Model:

ETANERCEPT or water orally administered as described above. Liver lymphocytes were prepared as described from all mice. One million cells were analyzed for the expression of CD4, CD8, CD25 and FOXP3. The numbers of purified CD4+CD25+, CD4+CD25+Foxp3, CD8+CD25+ and CD8+CD25+Foxp3 cells were calculated. Data are shown in table 4 as the mean percentage±SD in each group.

TABLE 4

Effect on regulatory T cells in hepatic distribution in ConA model

| Treg sub type | Cont, water | 0.1 mg ETANERCEPT |
|---|---|---|
| CD4+CD25+ | 6.6% ± 2.6 | 3.8% ± 2.5 |
| CD4+CD25+Foxp3+ | 2.3% ± 1.1 | 1.5% ± 0.9 |

TABLE 4-continued

Effect on regulatory T cells in hepatic distribution in ConA model

| Treg sub type | Cont, water | 0.1 mg ETANERCEPT |
|---|---|---|
| CD8+CD25+ | 3.1% ± 1.6 | 1.8% ± 1.1 |
| CD8+CD25+Foxp3+ | 13% ± 1.8 | 2.85% ± 3.1 |

Figure 4:
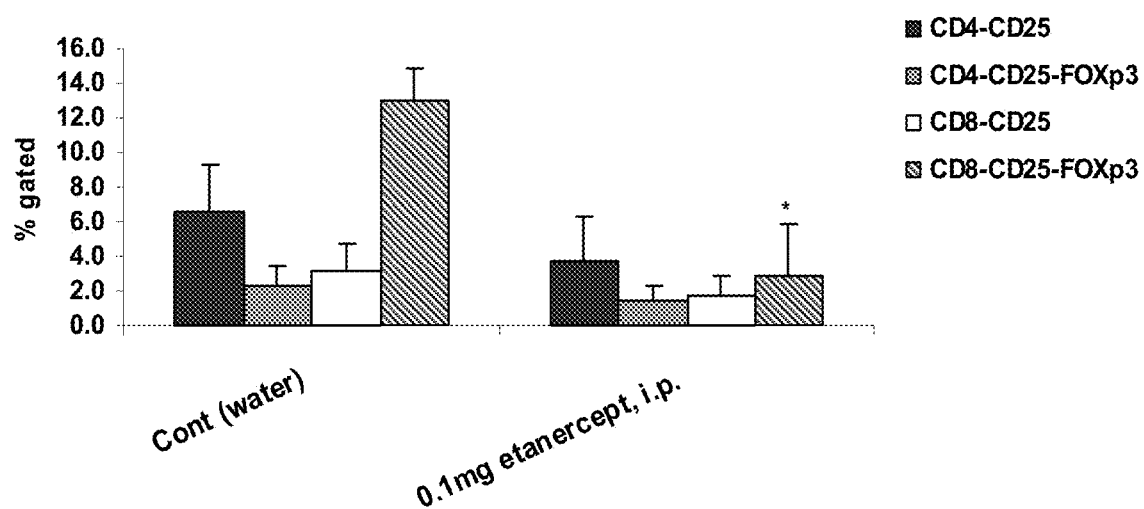
FIG. 4 is a bar graph showing that administration of 0.1 mg of ETANERCEPT resulted in a decrease of regulatory T cells (Tregs) in the liver of treated mice, compared to the administration of water only (significant results were obtained only in CD8+CD25+Foxp3+ cells, $p<0.008$).

As can be seen from the above table, administration of 0.1 mg of ETANERCEPT resulted in decrease of regulatory T cells (Tregs) in the liver of treated mice, compared to the administration of water only (significant results were obtained only in CD8+CD25+ Foxp3+ cells, p<0.008). These results are also presented in FIG. 4.

The Effect of ETANERCEPT on Splenic Tregs in ConA Model:

ETANERCEPT or water orally administered as described above. Splenocytes were prepared as described from all mice. One million cells were analyzed for the expression of CD4, CD8, CD25 and FOXP3. The numbers of purified CD4+CD25+, CD4+CD25+Foxp3, CD8+CD25+ and CD8+CD25+Foxp3 cells were calculated. Data are shown in Table 5 as the mean percentage±SD in each group.

TABLE 5

Effect on regulatory T cells in splenocytes distribution in ConA model

| Treg sub type | Cont, water | 0.1 mg ETANERCEPT |
|---|---|---|
| CD4+CD25+ | 8.8% ± 2.1 | 5.6% ± 0.4 |
| CD4+CD25+Foxp3+ | 2.6% ± 0.7 | 1.3% ± 0.2 |
| CD8+CD25+ | 2.7% ± 0.6 | 3.3% ± 1.6 |
| CD8+CD25+Foxp3+ | 8.0% ± 4.9 | 1.6% ± 0.5 |

Figure 5:
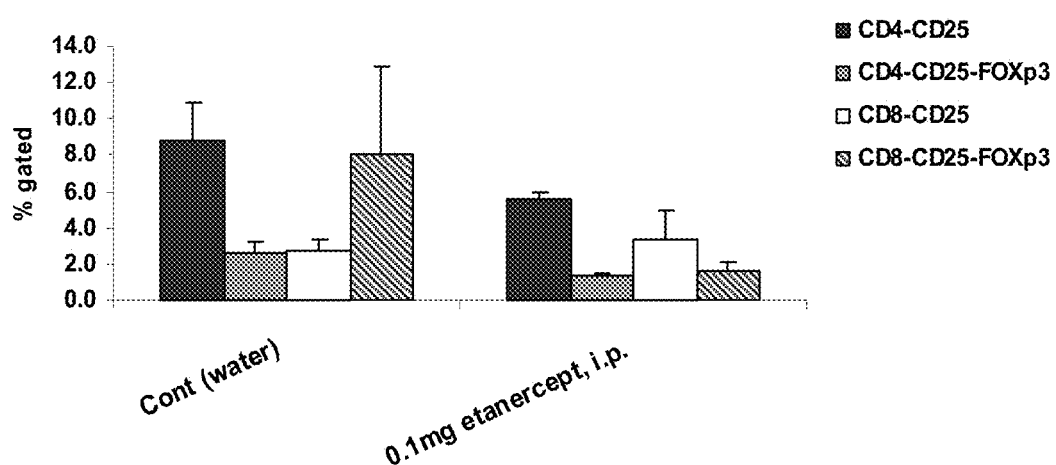
FIG. 5 is a bar graph showing that administration of 0.1 mg of ETANERCEPT resulted in decrease of regulatory T cells (Tregs) in the spleen of treated mice, compared to the administration of water only (significant results were obtained only in CD8+CD25+Foxp3+ cells, $p<0.008$).

As can be seen from the above table, the administration of 0.1 mg of ETANERCEPT resulted in decrease of regulatory T cells (Tregs) in the spleen of treated mice, compared to the administration of water only. These results are also presented in FIG. 5.

Experiment 3-PO Administration of ETANERCEPT

Experiment Protocol: per os administrations of between 0.001 ng and 1 g ETANERCEPT (treated mice) and water (control mice) are performed once a day for three consecutive days at various concentrations prior to ConA injection. Con A is and injected intravenously to tail vein of all mice. All mice are sacrificed. Sera from individual mice is obtained after ConA injection. The serum activities of ALT and AST is determined after dilutions, using a clinical chemistry analyzer. Serum levels of IFN-γ is determined using commercial kits, according to the manufacturer's instructions. After mice are sacrificed, livers and spleens from all mice are removed for the use of flow cytometry in order to detect changes in the expression of hepatic and splenic markers (regulatory T cells, Tregs).

Isolation of Splenocytes and Intrahepatic Lymphocytes: Livers and spleens are removed after sacrifice and stored. Spleens are crushed and centrifuged. Red blood cells are lysed. Splenocytes are washed and resuspended in. The viability of cells may exceeded 90%. For intrahepatic lymphocytes, livers are crushed through a stainless mesh. Lymphoprep is loaded with a similar volume of the cell suspension in tubes. The tubes are centrifuged. Cells present in the interface are collected and centrifuged again to obtain a pellet of cells depleted of hepatocytes. Approximately $1\times10^6$ cells/mouse liver may be recovered.

Flow Cytometry for Lymphocyte Subsets: Flow cytometry is performed following splenocyte and hepatic lymphocyte isolation using lymphocytes. For surface staining, cells are incubated with fluorochrome-conjugated antibodies to the indicated cell surface markers at the recommended dilutions or with isotype control antibodies. Cells are then washed in PBS and fixed with fixation buffer. For intracellular staining of Foxp3, fixed cells are permeabilized with Foxp3 staining buffer. Cells are then stained with PE-Cy7-conjugated antibodies to Foxp3, washed twice and resuspended in PBS and kept at 4° C. Stained cells in PBS are subsequently analyzed. Only live cells are counted, and background fluorescence from non-antibody-treated lymphocytes is subtracted.

We expect the results to be in line with the i.p. results of example 2. Namely, administration of ETANERCEPT will result in a reduction in the serum levels of ALT and of IFN-γ, compared to the administration of water only. It will also result in a decrease of regulatory T cells (Tregs) in the liver and spleen of treated mice, compared to the administration of water only.

What is claimed is:

1. A method for treating or reducing fatty liver disease or non-alcoholic steatohepatitis (NASH), in a subject in need thereof, the method comprising orally administering to the subject a therapeutically effective amount of pharmaceutical composition in a form of a liquid comprising a tumor necrosis factor (TNF) receptor fusion protein thereby treating or reducing the severity of fatty liver disease or NASH.

2. The method of claim 1, wherein the liquid is water.

3. The method of claim 1, further comprising a preservative.

4. The method of claim 3, wherein the preservative is benzyl alcohol.

5. The method of claim 1, wherein the TNF receptor fusion protein is etanercept.

* * * * *